(12) United States Patent
Honda et al.

(10) Patent No.: US 7,812,948 B2
(45) Date of Patent: Oct. 12, 2010

(54) DIFFERENT-KIND-OF-OBJECT DETECTOR EMPLOYING PLANE SPECTROMETER

(75) Inventors: Takayoshi Honda, Takatsuki (JP); Taichirou Nishiyama, Osaka (JP); Yasuyuki Suga, Yokohama (JP)

(73) Assignee: Astellas Pharma Inc., Tokyo (JP)

( * ) Notice: Subject to any disclaimer, the term of this patent is extended or adjusted under 35 U.S.C. 154(b) by 762 days.

(21) Appl. No.: 10/576,255

(22) PCT Filed: Oct. 15, 2004

(86) PCT No.: PCT/JP2004/015219

§ 371 (c)(1), (2), (4) Date: May 15, 2007

(87) PCT Pub. No.: WO2005/038443

PCT Pub. Date: Apr. 28, 2005

(65) Prior Publication Data

US 2008/0024778 A1    Jan. 31, 2008

(30) Foreign Application Priority Data

Oct. 17, 2003 (JP) .............................. 2003-357763

(51) Int. Cl.
*G01J 3/28* (2006.01)
(52) U.S. Cl. ........................................ 356/326; 356/72
(58) Field of Classification Search ................. 356/326, 356/300; 250/339.01, 338.1; 702/182, 135, 702/47
See application file for complete search history.

(56) References Cited

U.S. PATENT DOCUMENTS 5,724,437 A * 3/1998 Bucher et al. ............... 382/112
6,509,537 B1 * 1/2003 Krieg et al. .................. 209/579
6,587,575 B1 * 7/2003 Windham et al. ........... 382/110
6,894,772 B2 * 5/2005 Goetz et al. ............... 356/237.1
2002/0109835 A1   8/2002 Goetz
2005/0092941 A1 * 5/2005 Christiansen et al. .... 250/495.1

FOREIGN PATENT DOCUMENTS

EP    0 887 638    5/2003
JP    58-52551     3/1983

(Continued)

OTHER PUBLICATIONS

Imran Malik, et al., "Multispectral Imaging of Tablets in Blister Packaging", American Association of Pharmaceutical Scientists, XP009091875, vol. 2, No. 2, 2001, pp. 1-7.

(Continued)

*Primary Examiner*—L. G Lauchman
(74) *Attorney, Agent, or Firm*—Oblon, Spivak, McClelland, Maier & Neustadt, L.L.P.

(57) ABSTRACT

A detector for detecting a different kind of object among objects being carried with high resolution using a plane spectrometer irradiates near-infrared ray and performs plane spectroscopy for a reflected light. The detector also detects spectral data of the reflected light and performs preprocessing for averaging and standardizing the spectral data. Then wavelength axis averaging, Lagrangian interpolation and spatial axis averaging are performed. Conversion of first-order/second-order differentiation, smoothing and calculation of the main component score on the basis of previously obtained loading vector data is also performed. Then performing judgment of a different kind of object is performed.

11 Claims, 17 Drawing Sheets

FOREIGN PATENT DOCUMENTS

| | | |
|---|---|---|
| JP | 2-226027 | 9/1990 |
| JP | 6-41864 | 2/1994 |
| JP | 6-288925 | 10/1994 |
| JP | 6-288936 | 10/1994 |
| JP | 7-8760 | 2/1995 |
| JP | 10-48128 | 2/1998 |
| JP | 10-149473 | 6/1998 |
| JP | 2002-328088 | 11/2002 |
| WO | 93/21548 | 10/1993 |

OTHER PUBLICATIONS

Thorsten Herkert, et al., "One hundred percent online identity check of pharmaceutical products by near-infrared spectroscopy on the packaging line", European Journal of Pharmaceutics and Biopharmaceutics, XP004257229, vol. 51, No. 1, Jan. 2001, pp. 9-16.

P. K. Aldridge, et al., "Identification of Tablet Formulations Inside Blister Packages by Near-Infrared Spectroscopy", Applied Spectroscopy, XP001098336, vol. 48, No. 10, 1994, pp. 1272-1276.

* cited by examiner

Frequency

First Main Component

Frequency

Fig.11B

| Line 1 | Article A | | Article B | | Article C | | Article D | | Article E | |
|---|---|---|---|---|---|---|---|---|---|---|
| | First Main Component | Second Main Component | First Main Component | Second Main Component | First Main Component | Second Main Component | First Main Component | Second Main Component | First Main Component | Second Main Component |
| Average (m) | 430.2 | 285.1 | 474.9 | −505.5 | 203.2 | −7.1 | 438.3 | −134.7 | 506.6 | 326.2 |
| Standard Deviation (σ) | 23.3 | 20.7 | 16.2 | 36.7 | 16.1 | 19.2 | 20.3 | 37.0 | 29.9 | 24.1 |
| 5σ | 116.7 | 103.7 | 81.2 | 183.5 | 80.7 | 96.2 | 101.3 | 184.9 | 149.4 | 120.7 |
| m+5σ | 547.0 | 388.8 | 556.1 | −322.0 | 283.9 | 89.1 | 539.6 | 50.3 | 656.0 | 446.9 |
| m−5σ | 313.5 | 181.4 | 393.7 | −689.0 | 122.5 | −103.3 | 337.0 | −319.6 | 357.1 | 205.5 |

| Line 2 | Article A | | Article B | | Article C | | Article D | | Article E | |
|---|---|---|---|---|---|---|---|---|---|---|
| | First Main Component | Second Main Component | First Main Component | Second Main Component | First Main Component | Second Main Component | First Main Component | Second Main Component | First Main Component | Second Main Component |
| Average (m) | 396.7 | 237.4 | 382.3 | -431.1 | 174.4 | -0.2 | 383.1 | -127.9 | 478.5 | 260.7 |
| Standard Deviation (σ) | 21.0 | 16.5 | 15.5 | 33.0 | 16.4 | 17.9 | 16.9 | 28.1 | 24.0 | 17.5 |
| 5σ | 105.1 | 82.6 | 77.4 | 165.2 | 81.9 | 89.4 | 84.7 | 140.3 | 119.9 | 87.3 |
| m+5σ | 501.8 | 320.0 | 459.8 | -265.8 | 256.3 | 89.2 | 467.9 | 12.4 | 598.3 | 348.0 |
| m-5σ | 291.6 | 154.9 | 304.9 | -596.3 | 92.6 | -89.6 | 298.4 | -268.1 | 358.6 | 173.4 |

DIFFERENT-KIND-OF-OBJECT DETECTOR EMPLOYING PLANE SPECTROMETER

FIELD OF THE INVENTION

The present invention relates to an apparatus for detecting whether a different-kind-of-object having the same shape is mixing in objects to be detected (hereinafter referred to as "object") having a certain fixed shape, such as a pharmaceutical product (tablets, capsules, and the like), a rubber stopper, or the like, and more particularly relates to an apparatus for performing a total inspection of the objects to be conveyed in in-line system.

Further, the tablets include a plain tablet (or an uncoated tablet), a sugar coated tablet, and a film coated tablet (an enteric tablet, or the like), and the capsules include a hard capsule and a soft elastic capsule.

BACKGROUND ART

Since conventional different-kind-of-object detecting apparatuses utilize a point spectrometer, in which the spectroscopy is performed at a single point for the reflected light of the light irradiated to an object, a movable mechanism, such as a galvo-mirror is required so as to perform a spectroscopic analysis for the reflected light from the object to be conveyed not in a single line but in multiple lines. (Refer to the Patent Document 1.)

In this case, a camera for confirming a position of the object has to be separately prepared at an upstream side of the spectroscope so that the position of the object is confirmed, and an image processing apparatus for identifying the position of the object from the image taken by means of the camera has to be prepared.

In addition, in a case that the aforementioned movable mechanism, such as a galvo-mirror is not utilized, the spectroscopes for the number of the lines of object to be conveyed in the multiple lines are required.

Further, a plane spectrometer (refer to the Patent Document 2) by which the spectroscopy for the reflected light at a plurality of points can be simultaneously performed is proposed.

RELATED PATENT DOCUMENTS

Patent Document 1: EP 0 887 638 B1 Publication

Patent Document 2: WO 93/21548 Publication

DISCLOSURE OF THE INVENTION

In the case that the point spectrometer is used as the former, there has been a problem such that cost of the entire apparatus runs up. This is because the movable mechanism, such as a galvo-mirror, the camera for confirming the position of the object, and the image processing apparatus are required as described in the Patent Document 1.

In the case as the latter that the spectroscopes for the number of the lines of the object are used without utilizing the movable mechanism such as a galvo-mirror, there has been another problem such as that installation space is limited. This is because the installation space for these spectroscopes becomes extremely large.

Further, in the different-kind-of-object detecting apparatus described in the Patent Document 2, although the plane spectroscopy can be simultaneously performed, it is hard to directly use the same for the spectroscopic analysis in line. This is because resolution performance of the spectroscopic analysis thereof is in an extent of one tenth in comparison with that of the point spectroscopy.

Accordingly, the present invention is made in light of an object of solving the above-described problems, and providing an apparatus capable of detecting a different kind of object among objects to be conveyed at high resolution performance using a plane spectrometer.

DISCLOSURE OF THE INVENTION

To solve the above described problems, below described means is performed in the present invention.

Namely, the apparatus for detecting a different kind of object among objects using a plane spectrometer includes a conveying means for conveying a plurality of objects, a irradiating means for radiating near-infrared rays to the plurality of objects to be conveyed by means of the conveying means, a plane spectrometer that performs plane spectroscopy for a reflected light of the near-infrared rays reflected from the plurality of objects, to which the near-infrared rays are irradiated with the irradiating means, an imaging means for converting a plane spectrogram of the reflected light produced through the plane spectrometer into an electric signal by means of a near-infrared ray camera, and an analyzing means for detecting a different kind of object from the plurality of objects using a method of main component analysis upon obtaining spectral data of the reflected light by means of analyzing the electric signal obtained with the imaging means.

The analyzing means is configured to perform a wavelength axis averaging processing for averaging spectral data in a direction of the wavelength axis; an interpolation processing for interpolating the spectral data using Lagrangian secondary interpolation; a measuring position optimization processing for detecting a center position of the object by means of detecting an edge of the object upon accumulating the spectral data in a direction of a spatial axis; a spatial axis averaging processing for obtaining an average value of each of the wavelengths at a plurality of points in the vicinity of the center position of the object detected by means of the measuring position optimization processing; a differentiation processing for performing a first differentiation or a second differentiation for the spectral data; a main component score calculation processing for calculating the main component score by means of calculating previously obtained loading vector data and the spectral data obtained from the above-listed processes; and a determination processing for determining whether to be the a different kind of object or the same kind of object on the basis of the calculated main component score.

The wavelength axis averaging processing of the analyzing means is configured to perform at least any of a preprocessing for averaging the spectral data; a preprocessing for standardizing the spectral data on the basis of a ratio of the spectral data to a predetermined value; a preprocessing for standardizing the spectral data on the basis of a difference between the spectral data and a predetermined data; or the wavelength axis averaging processing for forming a moving average of the spectral data in the direction of the wavelength axis.

The analyzing means is configured to perform a conversion processing for smoothing the spectral data.

The analyzing means is also configured to perform a correction processing for the spectral data by means of MSC (Multiplicative scatter correction) method.

The analyzing means is also configured to detect abnormality of the object in a case that the edge exceeding a predetermined threshold cannot be detected in the measuring position optimization processing for detecting the center position of the object by means of detecting the edge of the object upon accumulating the spectral data in the direction of the spatial axis.

In this case, the abnormality of the object also includes a case that a shape is abnormal, or a case that the object does not exist at a predetermined position.

Further, the analyzing means is configured to perform the main component analysis for the object at each of the lines being conveyed in multiple lines, using the loading vector data created at each of the lines.

In addition, the analyzing means is configured to perform the main component analysis selecting only data of a predetermined wavelength band in the spectral data.

The analyzing means is also configured to perform a conditional branching processing while repeating for two or more times upon changing a condition of the main component analysis.

The imaging means is a rolling-type near-infrared ray camera, the rolling-type near-infrared ray camera having a camera rotating mechanism whereby the near-infrared ray camera can be rotated around a shaft in parallel with a light axis thereof.

The conveying means comprises a sheet-like conveying device for conveying the objects, the sheet-like conveying device having a flap-inhibitor for preventing a flap of the object by means of pressing a peripheral portion of the sheet-like conveying device around the object to be conveyed.

In the apparatus for detecting a different kind of object among objects using a plane spectrometer, a light volume compensator having a predetermined reflectance property is disposed at a position within a visual field of the imaging means.

In the present invention, since minute data having little noise is generated by means of using the plane spectrometer and performing the data interpolation and smoothing processing by the construction mentioned above, a resolution performance of the main component analysis by means of the spectral data is improved.

EFFECT OF THE INVENTION

A high resolution performance is obtained by means of using a plane spectrometer and performing processes, such as data interpolation, smoothing, and the like with characteristic algorithm. Further, a component analysis for a plurality of points across a wide area becomes to be able to be stably performed in line. Furthermore, since a spectroscopy for many points of the object being conveyed in multiple lines can be performed at the same time using one set of imaging means, space saving can be intended. In addition, since an attaching structure to a path for conveying the object to be measured can be formed extremely simple, a different kind of object detecting apparatus using a plane spectrometer can be easily attached to various conveying paths. Further, correction of imaging characteristic is completed at one time by means of using the one set of the imaging means.

The component monitoring in line for all the articles being conveyed becomes possible to be performed in a manner as described above, and shipping of the product having a stable quality where no different-kind-of-object is commingled becomes possible.

Since the aforementioned analyzing means is configured to detect abnormality of the object in a case that the edge exceeding a predetermined threshold cannot be detected in the aforementioned measuring position optimization processing of the analyzing means, a case that a shape is abnormal, or a case that the object does not exist at a predetermined position, for example, missing tablets can be detected.

Since the analyzing means is configured to perform the main component analysis for the object at each of the lines being conveyed in multiple lines, using the loading vector data created at each of the lines, the influence of the difference between the conditions such as the difference between the light volumes, or the like due to the difference between the lines in a case of conveying in multiple lines can be eliminated.

Further, since the analyzing means is configured to perform the main component analysis selecting only data of a predetermined wavelength band in the spectral data, accurate analysis can be performed by little amount of the data, and the load of calculating processing is decreased resulting in being capable of high speed processing.

Since the analyzing means is configured to perform a conditional branching processing while repeating for two or more times upon changing a condition of the main component analysis, even when a group, in which discrimination cannot be performed by means of the analysis in one condition, exists, the discrimination can be performed.

In addition, since the imaging means is a rolling-type near-infrared ray camera, the rolling-type near-infrared ray camera comprising an adjusting device for adjusting by rotating a shaft thereof, a deviation of a data bringing in timing can be compensated even in the case of the rolling-type near-infrared ray camera. In a case that the imaging means employed is not the rolling-type near-infrared ray camera, the adjusting device is not necessary.

Since the aforementioned conveying means comprises a sheet-like conveying device for conveying the objects, the sheet-like conveying device having a flap-inhibitor for preventing a flap of the object, it becomes possible to prevent a flap of the object to be conveyed by means of pressing a peripheral portion of the sheet-like conveying device around the object to be conveyed, and thereby it becomes possible to perform an accurate analysis. In a case that the object does not have a sheet-like shape, the flutter-preventing device is not necessary.

Furthermore, since a light volume compensator having a predetermined reflectance property is disposed in the vicinity of the object, a variation of the characteristics due to a change of properties with time, or the like can be compensated by means of controlling a light source or the imaging means in a manner such that the data obtained from the aforementioned light volume compensator is allowed to become a predetermined value.

BEST MODE FOR CARRYING-OUT OF THE INVENTION

FIG. 1 is a constructional view illustrating the embodiment of a different-kind-of-object detecting apparatus using a plane spectrometer of the present invention.

In the drawing, a numeral 1 denotes an apparatus for detecting a different kind of object among objects using the aforementioned plane spectrometer and is composed of a plane spectrometer 2, a near-infrared ray camera 3 serving as an imaging means, a light guide 4 serving as an irradiating means, a computer 5 serving as an analyzing means, and a conveying device 11.

The numeral 11 denotes an adsorption drum-type conveying device, described later, and this conveying device is configured to convey an object T such as, for example, tablet or the like being supplied from a hopper (not shown) by means of adsorbing onto a surface of an adsorption drum 12. As shown in the elevation in FIG. 2, at a surface of the aforementioned adsorption drum 12, the construction is formed such that a multiple-line conveyance is performed in a condition that a plurality of the object T are arrayed in a direction perpendicular to the conveying direction.

The aforementioned light guide 4 is configured to radiate the near-infrared rays to the lines of the object T as uniform as possible. Namely, the aforementioned light guide 4 is configured from a pair of the near-infrared ray light sources, in a manner so as to sandwich the line of the object T, and is disposed in a manner so as not to shade each object T, and further, to uniformly irradiate each object T. The position of the light guide 4 is arranged to be adjustable.

The aforementioned near-infrared ray light source can be constructed with, for example, a halogen lump, a near-infrared ray filter and a light introducing device such as an optical fiber bundle.

In addition, the aforementioned near-infrared ray camera 3 is provided with sufficient sensitivity to the region of the near-infrared ray having a wavelength from 900 to 1700 nm. Further, the numeral 6 denotes a light volume compensator and is fixed to a position to which the near-infrared ray is irradiated by means of the aforementioned light guide 4 in the same manner.

The aforementioned plane spectrometer 2 is disposed in a manner such that the reflected light of the near-infrared ray reflected from the object T is efficiently injected there into. Namely, the plane spectrometer 2 is disposed on an extension line of a radius connecting the object T to which the near-infrared ray is radiated and a center of the cross-section of the aforementioned adsorption drum 11 in a manner so as to train the light axis on the object T. The optic axis of the aforementioned plane spectrometer 2 is adjustably disposed.

The reflected light from the object T is injected into the aforementioned plane spectrometer 2, and light flux A (refer to FIG. 3) having a line-shaped cross-section in which a width in a conveying direction (a sub-scanning direction, i.e. a direction of an arrow Y) is minute, and in which a length in a conveying width direction (a main scanning direction, i.e., a direction of an arrow X) of the aforementioned adsorption drum 11 is large, is obtained. Further, by means of performing the plane spectroscopy for the light flux A, for example, a plane spectroscopic spectrum B (refer to FIG. 3) in which a horizontal axis corresponds to a position in the conveying width direction and a vertical axis corresponds to the wavelength is obtained. At a side in the vicinity of the plane spectroscopic spectrum B, spectral data to be a criterion obtained from the aforementioned light volume compensator 6 is also included.

Next, a construction in a case when a conveyer-type conveying device is used instead of using the aforementioned adsorption drum-type conveying device will be explained referring to FIG. 14.

In FIG. 14, the same numerals are attached to the same construction as that shown in FIG. 1, and the explanation thereof is omitted.

The numeral 13 denotes the conveyer-type conveying device and the conveyer-type conveying device is constructed such that the object T, such as for example, a tablet that is conveyed in multiple lines by being stored in a storing portion for the object in a resin sheet (PTP sheet) where the storing portion for the object is formed, is conveyed from a sending out roller to a receiving roller. As shown in an elevation in FIG. 15, the plurality of the object T are configured to be conveyed in the multiple lines in a condition of being arrayed in a direction perpendicular to the conveying direction by means of the aforementioned PTP sheet.

Incidentally, the numeral 6 denotes the light volume compensator and the light volume compensator 6 is fixed to a position, to which the near-infrared ray is irradiated by means of the aforementioned light guide 4, and to a position within a visual field of the aforementioned near-infrared ray camera 3 in the same manner as that of the aforementioned light guide 4.

The numeral 7 denotes a flutter-preventing plate and the flutter-preventing plate is fixed to the position to which the near-infrared ray is radiated by means of the aforementioned light guide 4, in the same manner as that of the aforementioned light guide 4, the light volume compensator 6, and the like. As shown in FIG. 18A, a through-hole 71 is formed in the flutter-preventing plate 7 so that the imaging for the object T is not disturbed. Accordingly, as shown in FIG. 18B, the object T conveyed by means of the PTP (press through pack) sheet can be imaged through the aforementioned throughhole 71.

In the plane spectrometer 2, for example, a plane spectroscopic spectrum B (refer to FIG. 3) in which the horizontal axis corresponds to the position in the conveying width direction and the vertical axis corresponds to the wavelength is obtained, as described above.

Incidentally, since the reflected light of the near-infrared ray from the object is transmitted through a film of the PTP sheet, the existence or absence of a different-kind-of-object can be detected from above the film of the PTP sheet.

The object is configured to be conveyed in multiple lines by means of the thus described adsorption drum-type or a conveyer-type conveying device.

Further, plane spectral data obtained by means of the aforementioned plane spectrometer 2 is formed to be an image on an imaging surface of the near-infrared ray camera 3, and is converted into an electric signal by means of, for example, a CCD element, or the like imaging device. The electric signal is further converted into a digital signal and is transmitted to the aforementioned computer 5.

Incidentally, the digital signal is preferable to be configured to be transmitted to the aforementioned computer 5 by capturing the image in synchronization with the trigger signal obtained at the timing when the object conveyed by means of the aforementioned conveying device reaches a predetermined position.

In the computer 5, the transmitted spectral data is processed by means of newly developed algorithm, described later, and the object T is discriminated between a non-defective object and a different kind of object.

The later described algorithm is the one using a main component analysis which is one of a chemometrics being effective for the spectrum analysis.

The algorithm that serves as an analyzing means at the aforementioned computer 5 includes the following processes:

1) Preprocessing for averaging and standardizing the aforementioned spectral data
2) Wavelength axis averaging processing for forming a moving average from the aforementioned spectral data in a direction of the wavelength axis
3) Interpolation processing for interpolating the aforementioned spectral data using Lagrangian secondary interpolation
4) Measuring Position Optimization Processing for detecting a center position of a object by means of detecting an edge of the object, accumulating the aforementioned spectral data in a direction of spatial axis 5) Spatial Axis Averaging Processing for obtaining average value of each of the wavelengths at a plurality of points in the vicinity of the center position of the object detected by means of the aforementioned measuring position optimization processing
6) Differential Processing for performing first differentiation of the aforementioned spectral data or second differentiation of the same
7) Processing for smoothing the aforementioned spectral data, and for correcting the same by means of MSC method
8) Main Component Score Calculation Processing for calculating the main component score by means of computing previously obtained loading spectral data and the spectral data obtained by the above-described processing
9) Determination Processing for determining whether to be a different-kind-of-object or the same-kind-of-object on the basis of the calculated main component score
10) Defective Object Detection Processing for performing detection for the defective object by means of utilizing the measuring position optimization processing
11) Conditional Branching Processing Further, the order of the processes is not limited to that described above.

Next, calculating method for each of the aforementioned processes will be explained in detail.

1) Preprocessing (Averaging and Standardizing)

At least any of the processes, such as the averaging, ratio standardization, and difference standardization, described below, is performed. (It may be performed after performing the spatial axis averaging processing, described later.)

It is effective to use the averaging and the difference standardization at the same time.

Averaging: A processing in which the average value of the spectral data is subtracted from each of the data of the wavelength and then is converted into positive and negative data Ratio Standardization: A processing in which the spectral data is standardized on the basis of a ratio of the spectral data and a predetermined value In concrete terms, this is a processing in which the data of each of the wavelengths is divided by standard deviation of the spectral data and is thereby standardized, and an effect of variation among each of the spectral data is eliminated.

Difference Standardization: A processing in which the spectral data is standardized on the basis of the difference between the spectral data and a predetermined value In concrete terms, this is a processing in which the difference between the standard deviation of the spectral data and the data of each of the wavelengths is obtained and is standardized, and the effect of variation among each of the spectral data is eliminated.

2) Wavelength Axis Averaging Processing

An effect of a slight noise riding on a waveform is decreased by means of forming moving average in three to twenty points in a direction of a wavelength axis of a graph showing a reflectance ratio in the vertical axis and a wavelength in the horizontal axis.

3) Lagrangian Interpolation Processing

The spectral data obtained at intervals of about 4 mm is interpolated into minute data at intervals of 2 mm using the Lagrangian interpolation of secondary or more of interpolation.

4) Measuring Position Optimization Processing

An accumulation value is calculated by accumulating a reflectance ratio at each of the points in a direction of spatial axis, and the profile (refer to FIG. 4A) showing the accumulation value in the vertical axis and the number of points of the spatial axis in the horizontal axis is multiplied by the first differentiation. Further, the maximum value and the minimum value are recognized as edges (namely, edges) of the object (refer to FIG. 4B), and a center position and a radius are obtained from a middle point between both of the edges (refer to FIG. 4C).

5) Spatial Axis Averaging Processing

An average value of the reflectance ratio at each of the wavelengths to an extent of an arbitrary number of the points from the center of the object to the edge of the object obtained by means of the aforementioned measuring position optimization processing of the article No. 4 is obtained. By means of this processing, the spectral data, not based on the light reflected from only a single point of the object, but based on an average value of the light reflected from a plurality of points of the object can be obtained.

6) Conversion Processing (First Differentiation or Second Differentiation, and Smoothing)

The first differentiation or the second differentiation is performed so as to emphasize absorption peak of the spectral data. Further, the smoothing is performed at every several to several dozen of points so as to decrease the effect of the noise. The Savitzky-Golay's least-squares method, for example, is used for the first differentiation or the second differentiation, and smoothing. Otherwise, it is effective for eliminating the effect of light scattering or the like to perform the correction processing by means of MSC method.

7) Main Component Score Calculation Processing

A main component analysis is previously performed using all samples to be detected and the loading vector data is obtained. Matrix calculation is performed as below described equation for the loading vector data and the spectral data, to which the interpolation, the preprocessing, and the conversion are performed by means of the above-described processes, and thereby the main component score is calculated in line. The calculated main component score is plotted on the main component analysis (hereinafter referred to as PCA, Main Component Analysis) diagram of one or more dimensions.

$$S = X \cdot La$$

S: main component score, X: Spectral data, La: Loading vector

In general, although it is sufficient to perform the main component analysis of two dimensions, the main component analysis of two or more dimensions can be performed.

8) Determination Processing

The data that is judged to be a non-defective object when the data plotted on the PCA diagram is within a previously set region of the non-defective object, and the data that is judged to be a different-kind-of-object when the data is outside the previously set region of the aforementioned non-defective object are sent to a sorting device or the like.

9) Defective Object Detection Processing

A threshold value is set to the maximum value of the waveform obtained by multiplying the profile used in the aforementioned measuring position optimization processing of the article No. 4 by the first differentiation, and the data less than the threshold value is detected as a defective object. (Refer to FIG. 5.)

In a case that the defective object is detected, even when other processes remain unexecuted, these processes are omitted to be perform and the detected physical article is judged to be a defective object.

10) Conditional Branching Processing

In a case that a plurality of samples to be detected exist and the plurality of samples cannot be discriminated by means of only one PCA diagram, the main component analysis is performed for a plurality of times by means of the conditional branching processing. The conditional branching processing is defined as a processing method in which the samples are separated into groups of a different kind of objects at the first time of the main component analysis, and then, the main component analysis is performed for each of the groups of products in the condition different from that of the first time. Repeating the same processing for three to four times and all the different kind of objects is discriminated.

Next, a brief procedure for performing the total detection in line by means of the different kind of object detecting apparatus using the plane spectrometer of the present invention will be explained below.

1) First, a PCA diagram relevant to all kinds of the object to be judged whether to be the same kind of object or the different kind of object is previously prepared.

In this case, all of the measured wavelengths are not included in the objects to be calculated, but only the wavelengths, in which the spectrum of the non-defective object has a significant difference compared to that of the a different kind of object, are included in the object to be calculated, and thereby the PCA diagram having a high accuracy of detection can be created.

Further, when the variation of the data among the lines is increased as a result of detecting a plurality of lines by means of using a PCA diagram, the accuracy of detection can be improved by making the PCA diagram for every line.

2) The region of the non-defective object is set to the PCA diagram after the PCA diagram is created, and an evaluation chart is created.

When in-line detection is performed, the evaluation chart and the loading vector obtained when the PCA chart is created are used.

3) In the in-line detection, the averaging, the smoothing, and the interpolation processing are performed for the obtained spectral data first, and then the defective object detection is performed. In a case that the spectral data passes the defective object detection, the measuring position optimization processing is performed, and the preprocessing and the conversion processing are performed thereafter.

4) The main component score is calculated by means of performing the matrix calculation for the loading vector, obtained when the PCA diagram is created, and the obtained spectral data, so as to perform the main component analysis for the spectral data. By means of adopting this method, the in-line detection using the main component analysis becomes capable of performing.

5) The calculated main component score is plotted on the evaluation chart that is previously drawn up, and right and wrong judgment is performed.

In a case that the object cannot be discriminated by performing the above described main component analysis for one time, the main component analysis is repeated after processing by the aforementioned conditional branching method while changing the condition including the changing of the wavelength to be the object of calculating, or the number of times of performing the differentiation.

As described above, since the aforementioned algorithm for use in the a different kind of object detecting apparatus using the plane spectrometer of the present invention has a little computational effort, the cycle time required for calculation processing is short (several milliseconds for one-time processing).

Accordingly, even when the main component analysis is repeated for many times performing the conditional branching processing, the aforementioned object can be fully achieved at a short time.

Next, a camera rotating mechanism for adjusting positions of the plane spectrometer and the near-infrared ray camera will be explained.

In a case that an imaging system of the camera employed is a rolling-type, since the data is sequentially read in on a cell to cell basis of an imaging device, the reading in timing for the last cell data delays from that for the first cell data for a dozen or more milliseconds. Accordingly, if nothing is done, deviation occurs at a measuring point corresponding to a position of a conveying line, and therefore the same position of each of the objects in all the measuring lines cannot be measured. For example, even when a reflected light from a center position in a surface of the object is intended to be measured, depending on a conveying position of the object, the position that is deviated from the center of the object, namely a reflected light from a position having different reflection characteristics is measured.

Therefore, as shown in FIG. 16A, it is preferable that a camera rotating mechanism 8 so as to rotate the plane spectrometer 2 and the near-infrared ray camera 3 around a shaft in parallel with the optical axis is provided. The camera rotating mechanism 8 is configured to rotate a mound portion 82 of the plane spectrometer 2 and the near-infrared ray camera 3 relative to a base portion 83 in a direction indicated by an arrow by means of rotating a finger grip 81.

For example, as shown in FIG. 16B, when a main scanning direction is defined as a direction of an arrow X, and a sub-scanning direction is defined as a direction of an arrow Y, in a case that a deviation (d) of the measuring point occurs at the objects at both ends of the conveying lines, the plane spectrometer 2 and the near-infrared ray camera are rotated around the shaft (including the optical axis) being in parallel with the optical axis, at an angle (θ) that is corresponding to the deviation amount of the aforementioned measuring point, by means of operating the aforementioned camera rotating mechanism 8.

Thus, by adjusting to an appropriate angle (θ) for compensating the deviation (d) of the aforementioned measuring point by means of the aforementioned camera rotating mechanism 8, the deviation of the aforementioned reading in timing is absorbed, and the center of the object in all of the conveying lines becomes capable of being measured.

Further, even when the light volume of the near-infrared ray or a sensitivity of the imaging device is changed along with elapse of time, the reflected light from the aforementioned light volume compensator 6 is configured to correct by means of automatic following.

Namely, before using the present apparatus, when reference data for each of the measuring points for use in a correction is obtained by measuring a white color board to be a criterion, the data of each wavelength of the reflected light from the light volume compensator 6 is obtained at the same time as first data, and at a time of measuring, the data of each wavelength of the reflected light from the light volume compensator 6 is obtained on an as-needed basis as second data. The light volume correction is performed by means of reflecting the rate of change of the second data relative to the first data to the reference data of each of the measuring points.

Further, the light volume correction can be also performed by following procedure. As shown in FIG. 17, a light volume correction circuit 9 is provided, and spectral data of the reflected light from the aforementioned light volume compensator 6 is brought into a comparison circuit 91 at every measuring time, and is compared to a criterion measure. Then, a control signal for correction is outputted from a conversion circuit 92. Further, the light volume of a light source of the aforementioned light guide 4 is configured to be varied by means of controlling a light source driving circuit 93 by the control signal for correction such that the aforementioned spectral data is brought to be a predetermined level.

Incidentally, below described construction can also be applicable. Namely, an optical fiber array composed of a plurality of optical fibers is disposed between the objects to be conveyed in a plurality of lines and the plane spectrometer, and one end side of each of the optical fibers is faced to the objects of each of the lines. The other end of each of the optical fibers is bound up and is faced to the plane spectrometer. The reflected light from the objects of each of the lines is injected into the optical fiber that faces each of the objects and introduced into the plane spectrometer.

Embodiment 1

Next, an embodiment, in which the a different-kind-of-object detecting apparatus using the plane spectrometer of the present invention is applied to five kinds of tablet articles (A, B, C, D, and E) as the object to be detected to which PTP packaging (7 lines) is performed using the conveyer-type conveying device, is shown.

First, 280 tablets are applied as the object using data of 40 tablets in each of the lines for each of the articles, so as to calculate the loading vector data for the main component score calculation processing. In 280 tablets, 90 tablets (3 lines) include a printed surface or a surface having an engraved mark.

The measuring condition in this embodiment is as follows:

| | |
|---|---|
| Used Lens: | f = 25 mm |
| Number of Points for Moving Average in Wavelength Axis: | 3 points |
| Wavelength for Statistical Processing: | 1000 to 1600 nm |
| Lagrangian Interpolation: | 2 nm |
| Smoothing: | Secondary |
| First Differentiation: | Secondary |
| Processing before Statistics: | Averaging and Standardization |
| Average Number of Spatial Axis: | 5 |
| Moving Speed: | 4.4 m/min |
| Number of Conveying Lines: | 7 lines |

In this Embodiment 1, the measured data is as follows:

1. Calculation of the Loading Vector (1) Obtaining Spectroscopic Spectrum

In the aforementioned condition, an image of the flat shaped spectral data taken by means of using a plane spectrometer (made by SPECIM, Spectral Imaging Ltd. in Finland) and a near-infrared ray camera (made by Sensors Unlimited, Inc. in U.S.A.) is shown in FIG. 6.

In FIG. 6, a lateral direction on the paper surface indicates a wavelength axis and a vertical direction on the paper surface indicates a spatial direction.

Nos. (1) through (7) show spectral data of reflected lights at 7 lines (lines 1 through 7) where the multiple-line conveyance is performed, and a white color portion (8) at the lowermost part shows a spectral data of a reflected light from the light volume compensator 6 being composed of a white color piece.

In this case, the calculation of the loading vector that has a high identifying power is performed using the data of the line 7 that has a bad condition due to the variation of the light volume, a fluttering of the sheet, or the like.

(2) Selection of a Frequency Band

A PCA diagram (FIG. 8) in a case of using an entire frequency area, and another PCA diagram (FIG. 10) in a case of selecting four wavelength-bands (star mark) as in FIG. 9, so as to obtain the loading vector data having the high identifying power, on the basis of the spectral data (the lateral axis serves as the wavelength axis) in FIG. 7 are shown.

In a case that the frequency band is not selected as in FIG. 9, it is hard to discriminate to each other because the data of each kind of the objects is not separated as shown in FIG. 8. However, in a case that the frequency band is selected as shown in FIG. 9, the corresponding articles, B, C, and D, can be determinately discriminated to each other as shown in FIG. 10 because the areas B, C, and D, in the areas A, B, C, D, and E, are not overlapped on each other. (As for the articles, A and E, it is hard to discriminate because the areas, A and E, are overlapped on each other.)

Thus, in a case that the articles (articles, A and E) that are hard to discriminate exist, it is preferable to perform the main component analysis for the data of another frequency band using the above-described conditional branching processing, or to discriminate by means of using another indicator, such as color, or the like, as described later.

2. Verification

The inventor verified as follows by performing in-line measuring for each of the articles of 300 tablets using the loading data and the evaluation sheet (setting a rectangular area formed of a first component and a second component) calculated as described above.

The data of the lines, 1 and 2, are selected from the data at a time of measuring the lines, 1 through 7, and the PCA diagram of that case and the respective numeric data of the average value (m), the standard deviation ($\sigma$), the average value+5$\sigma$, and the average value−5$\sigma$ are shown in FIGS. 11 and 12.

According to the data of the line 1 (in FIGS. 11A and 11B), the articles B, C, and D can be determinately discriminated to each other (articles, A and E are hard to discriminate).

According to the data of the line 2 (in FIGS. 12A and 12B), although the article C can be determinately discriminated from others, the articles, B and D, cannot be directly discriminated. That is, the area of the average value of the second component of the article B+5$\sigma$, and the area of the average value of the second component of the article D−5$\sigma$ are slightly overlapped (star mark) (as for the articles, A and E, it is hard to discriminate).

Incidentally, as for the PCA diagram in a case of the lines, 3 through 7, and the respective numeric value data, the illustration and the explanation are omitted.

3. Study

When the rectangular area composed of the first component and the second component is set as described above, part of the overlapped area occurs as the case of the line 2. However, as shown in FIG. 13, the occurrence of the overlapped part can be prevented by means of setting ellipse areas R1 and R2 each of which has a long axis and a short axis respectively formed from the first component and the second component, and thereby the discrimination becomes able to be performed to each other.

Further, in the above-described embodiment, since the article A and the article E have tablet-colors that are different to each other, they can be easily discriminated by means of using a color sensor.

As described above, in this embodiment, by means of combining the different-kind-of-object detecting apparatus using the plane spectrometer of the present invention and the color sensor, all of the five articles were able to be discriminated.

BRIEF DESCRIPTION OF THE DRAWINGS

FIG. 11 is data of the embodiment, in which FIG. 11B is an illustration showing numeric value data of line 1;

FIG. 12 is data of the embodiment, in which

FIG. 18 is a detailed explanatory view explaining a flutter-preventing plate, in which

Figure 1:
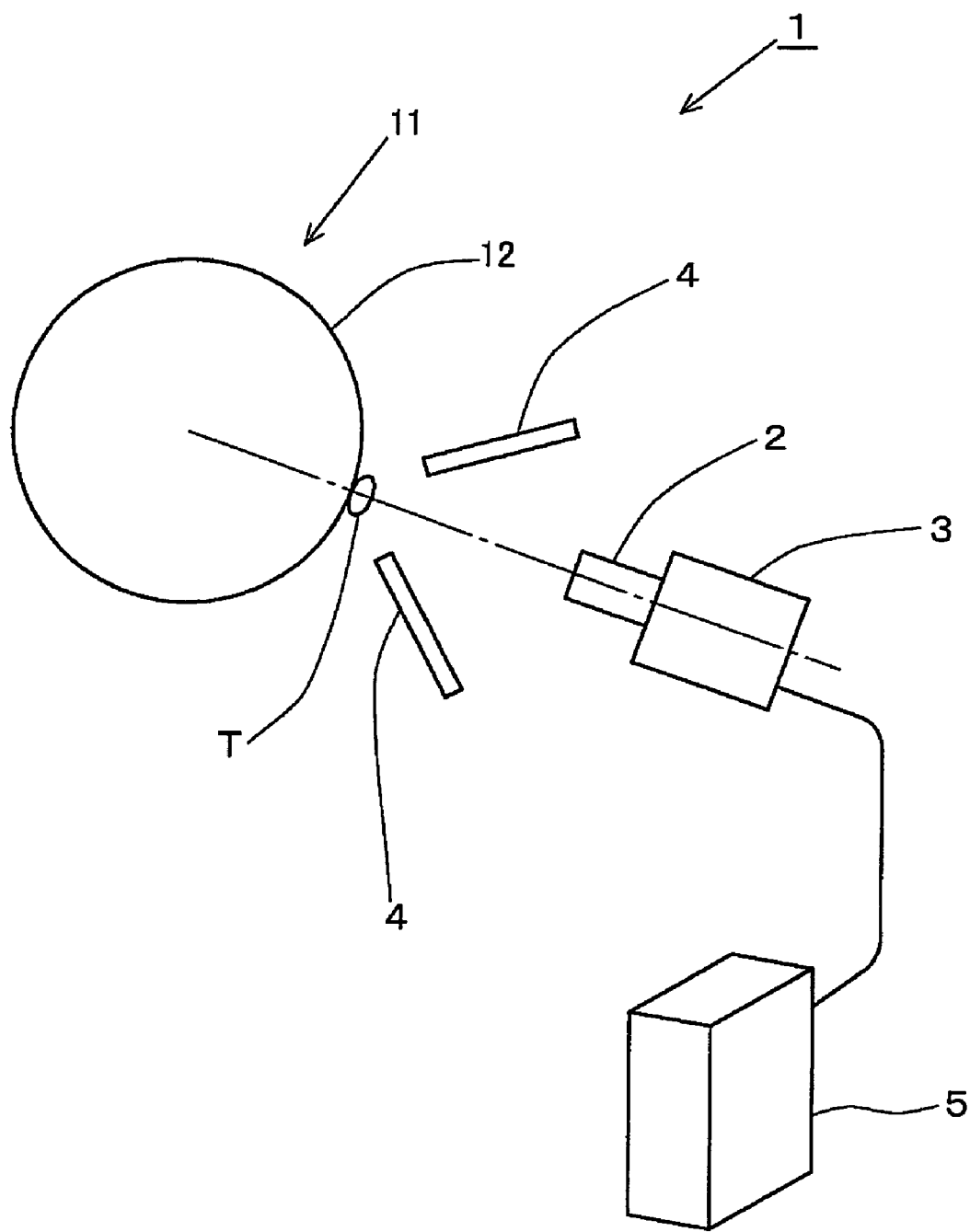
FIG. 1 is a side configuration view showing an embodiment of a different-kind-of-object detecting apparatus (adsorption drum-type) using a plane spectrometer with respect to the present invention.
Figure 2:
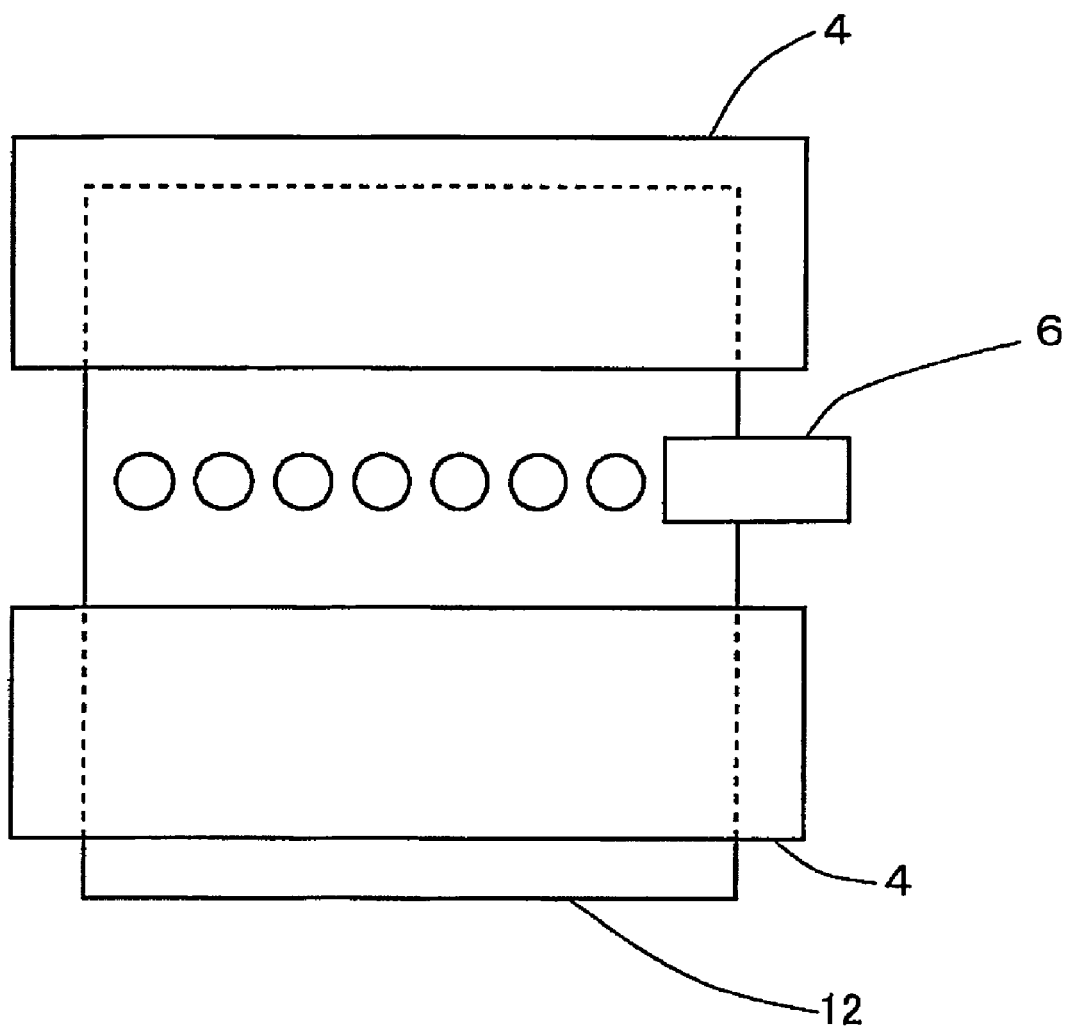
FIG. 2 is a plan configuration view showing a main part of the aforementioned embodiment.
Figure 3:
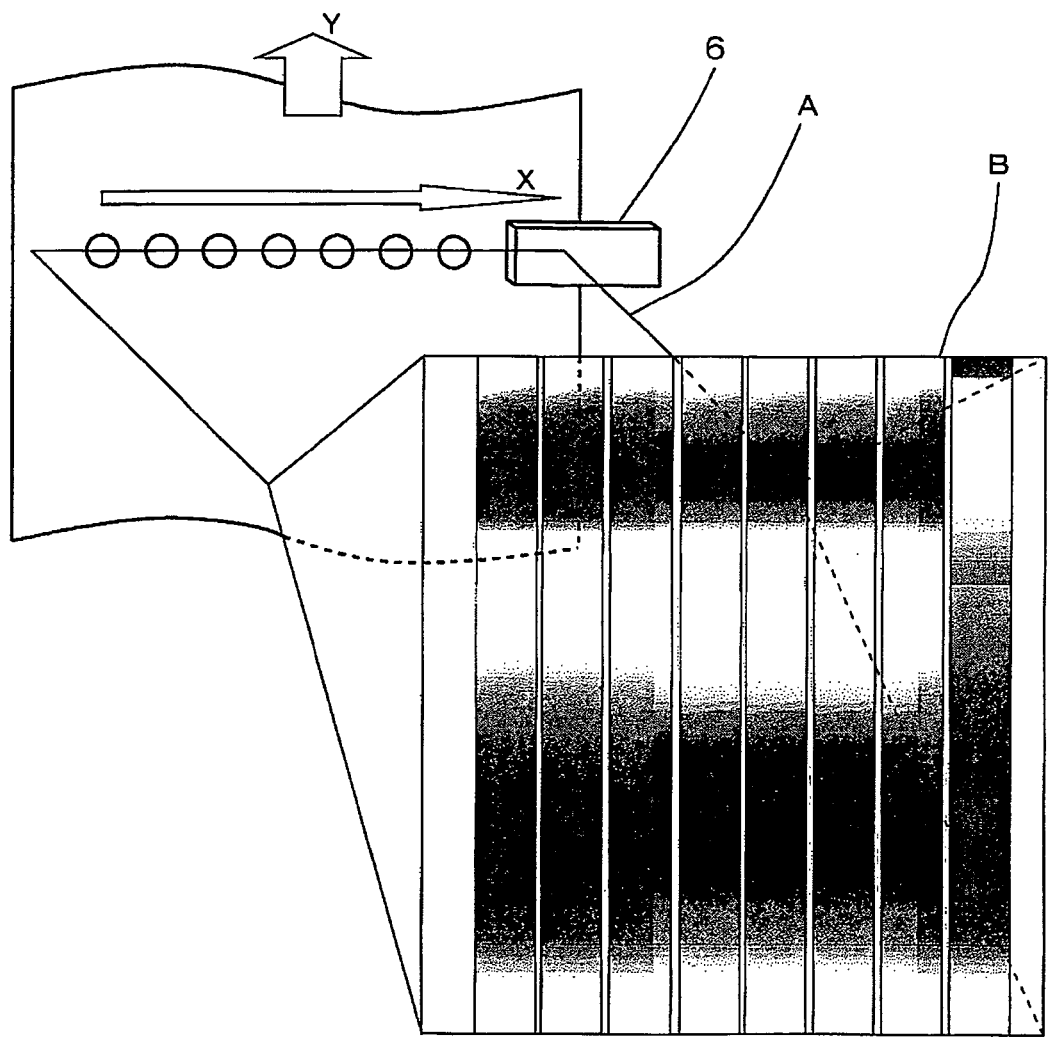
FIG. 3 is an explanatory view explaining a function of the plane spectrometer.
Figure 4A:
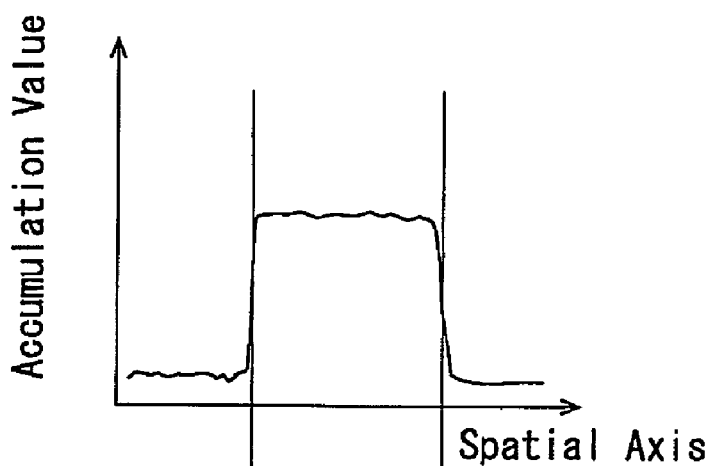
FIG. 4 is an explanatory view explaining a part of a measuring position optimization processing in an analyzing device, in which FIG. 4A explains a waveform of a profile, FIG. 4B explains a waveform resulting from detection of an edge by performing differentiation processing, and FIG. 4C explains a calculation of a center position and a radius.
Figure 4B:
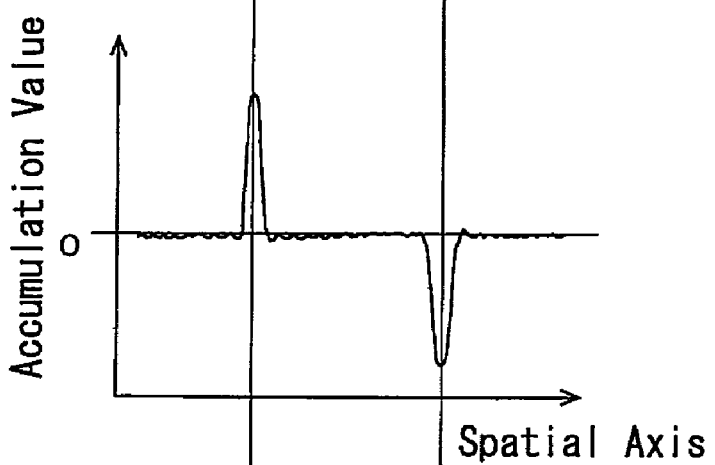
Figure 4C:
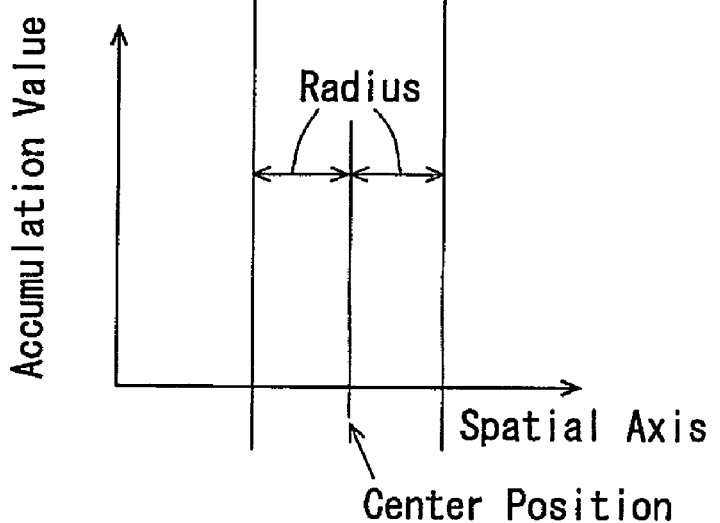
Figure 5:
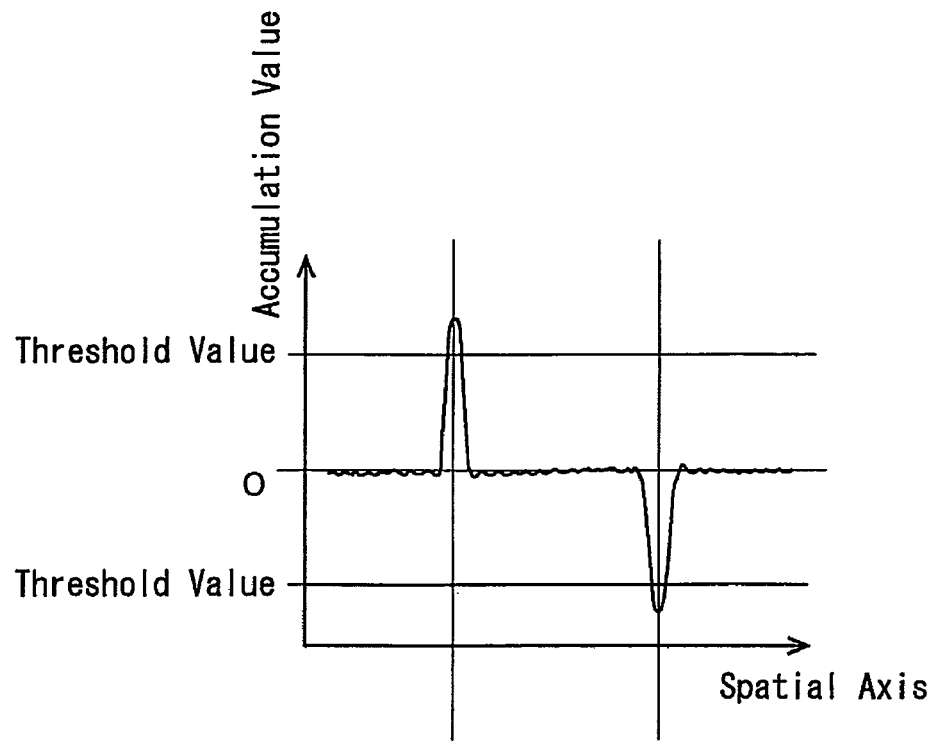
FIG. 5 is an explanatory view explaining a defective object detection processing in the aforementioned measuring position optimization processing.
Figure 6:
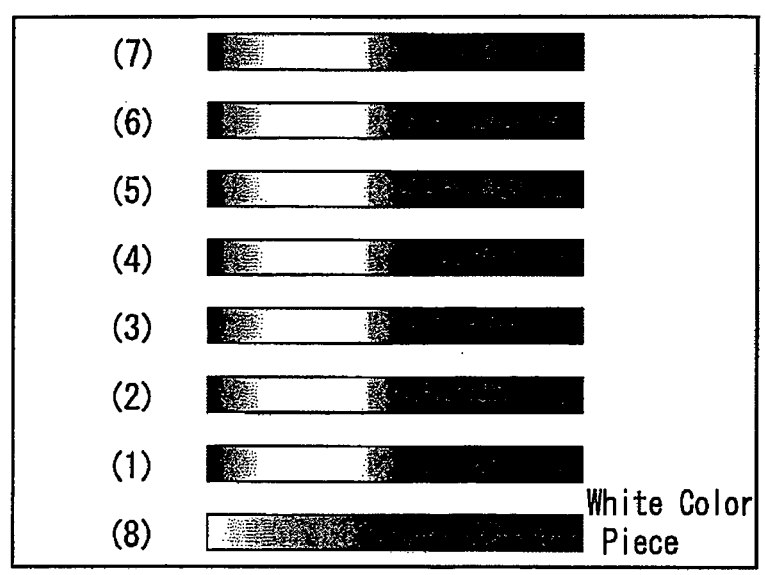
FIG. 6 is an illustration showing an example of spectra in which spectroscopy is performed in a plane of two dimensions.
Figure 7:
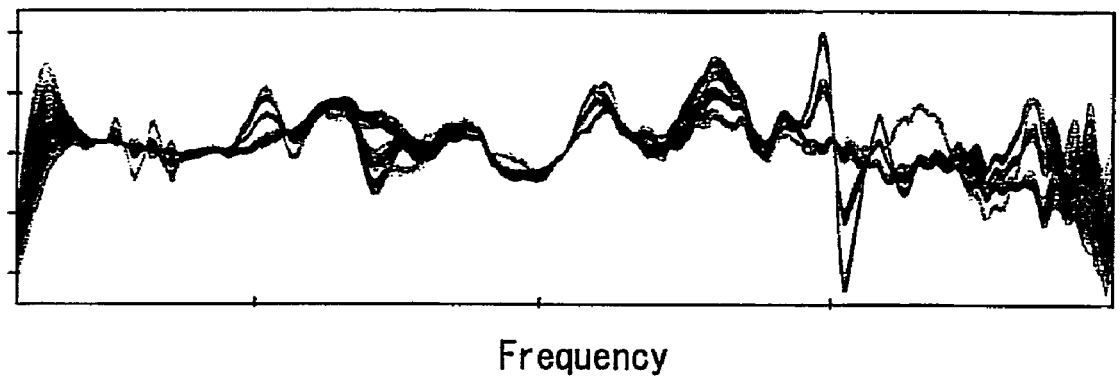
FIG. 7 is an illustration showing a spectrum of line 7 in the spectra of FIG. 6.
Figure 8:
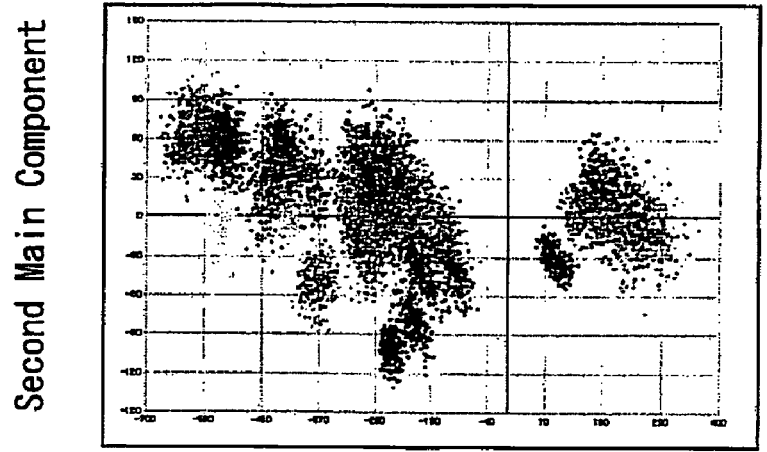
FIG. 8 is a PCA diagram based on the spectral data of FIG. 7.
Figure 9:
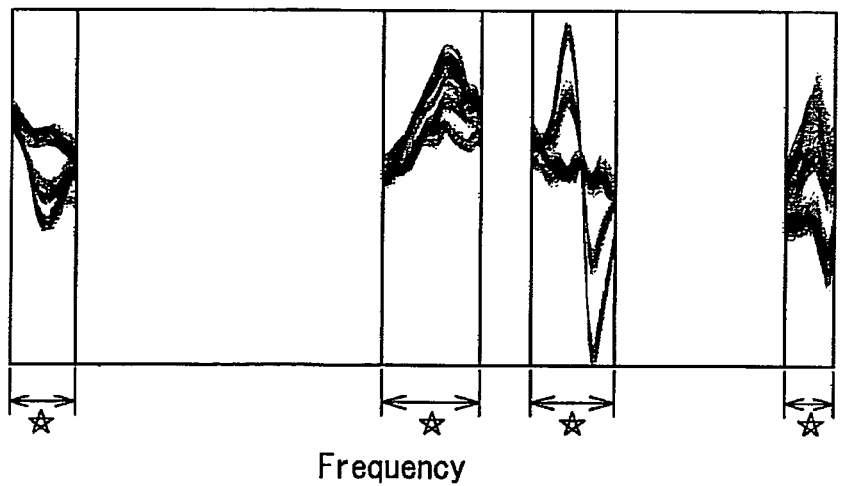
FIG. 9 is an illustration showing a spectrum in which four wavelength-bands are selected from the spectrum diagram of FIG. 7.
Figure 10:
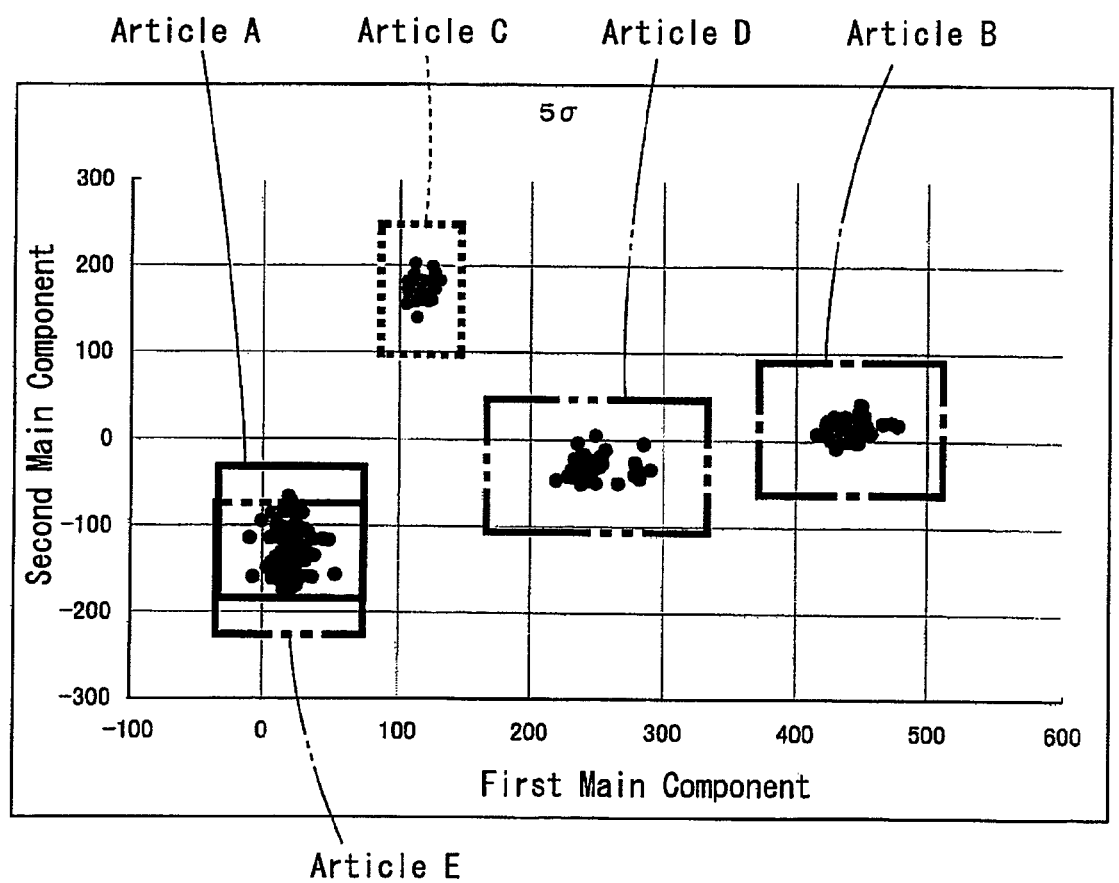
FIG. 10 is a PCA diagram based on the spectral data of FIG. 9.
Figure 11A:
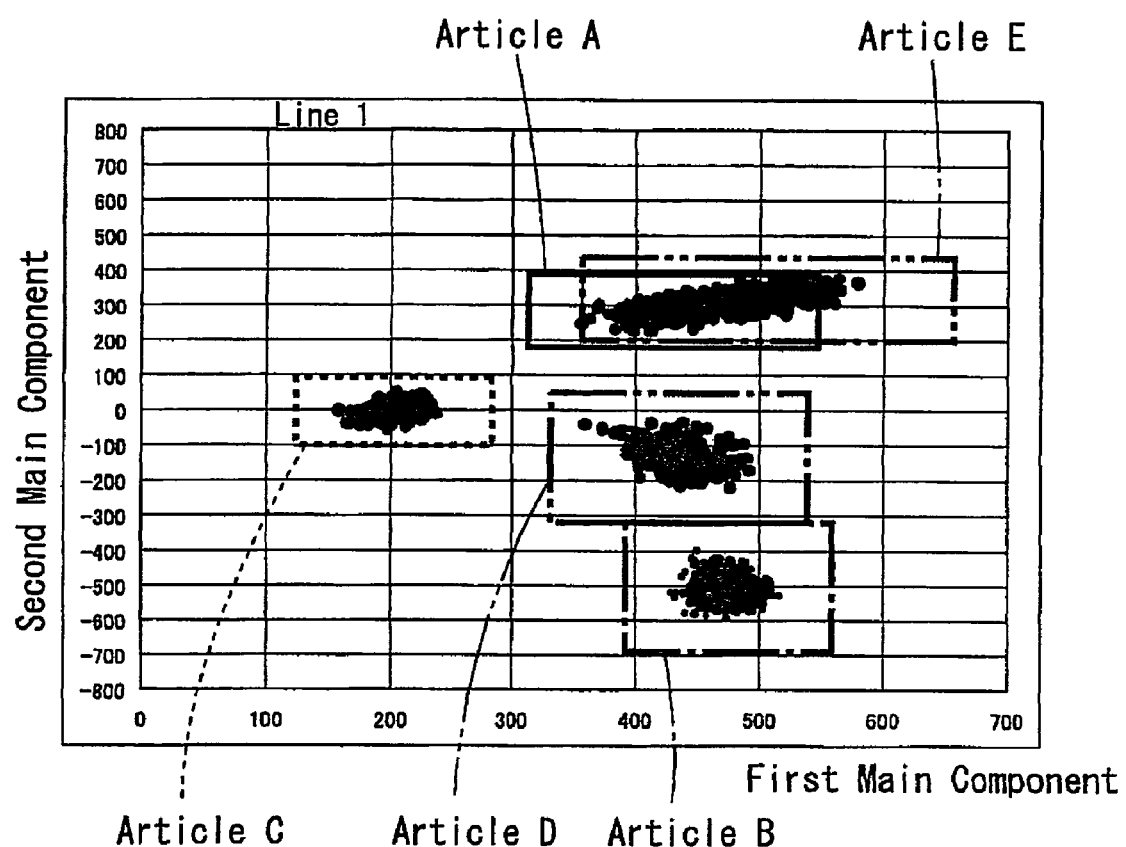
FIG. 11A is a PCA diagram of line 1.
Figure 12A:
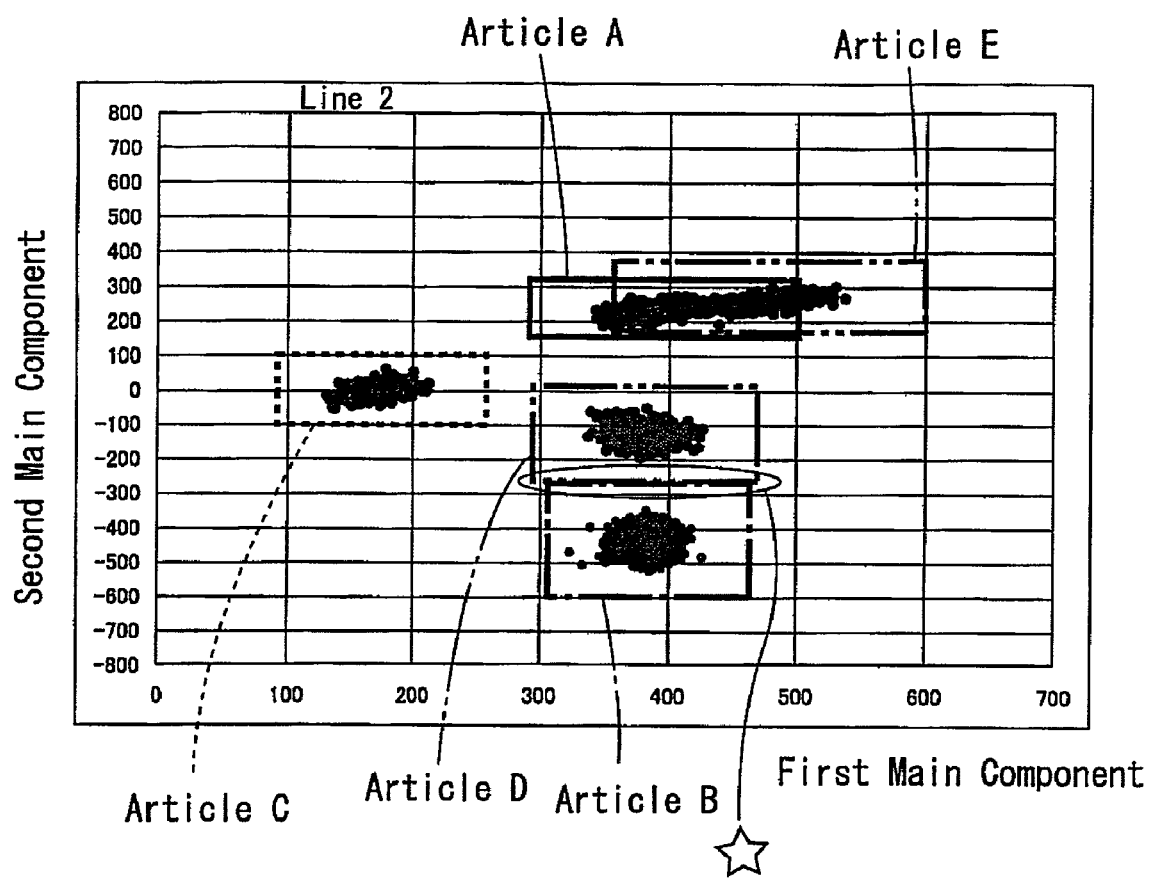
FIG. 12A is a PCA diagram of line 2.
Figure 12B:
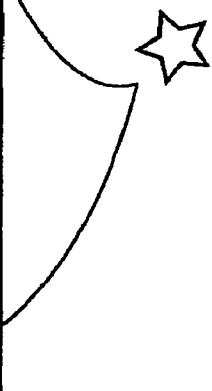
FIG. 12B is an illustration showing numeric value data of line 2.
Figure 13:
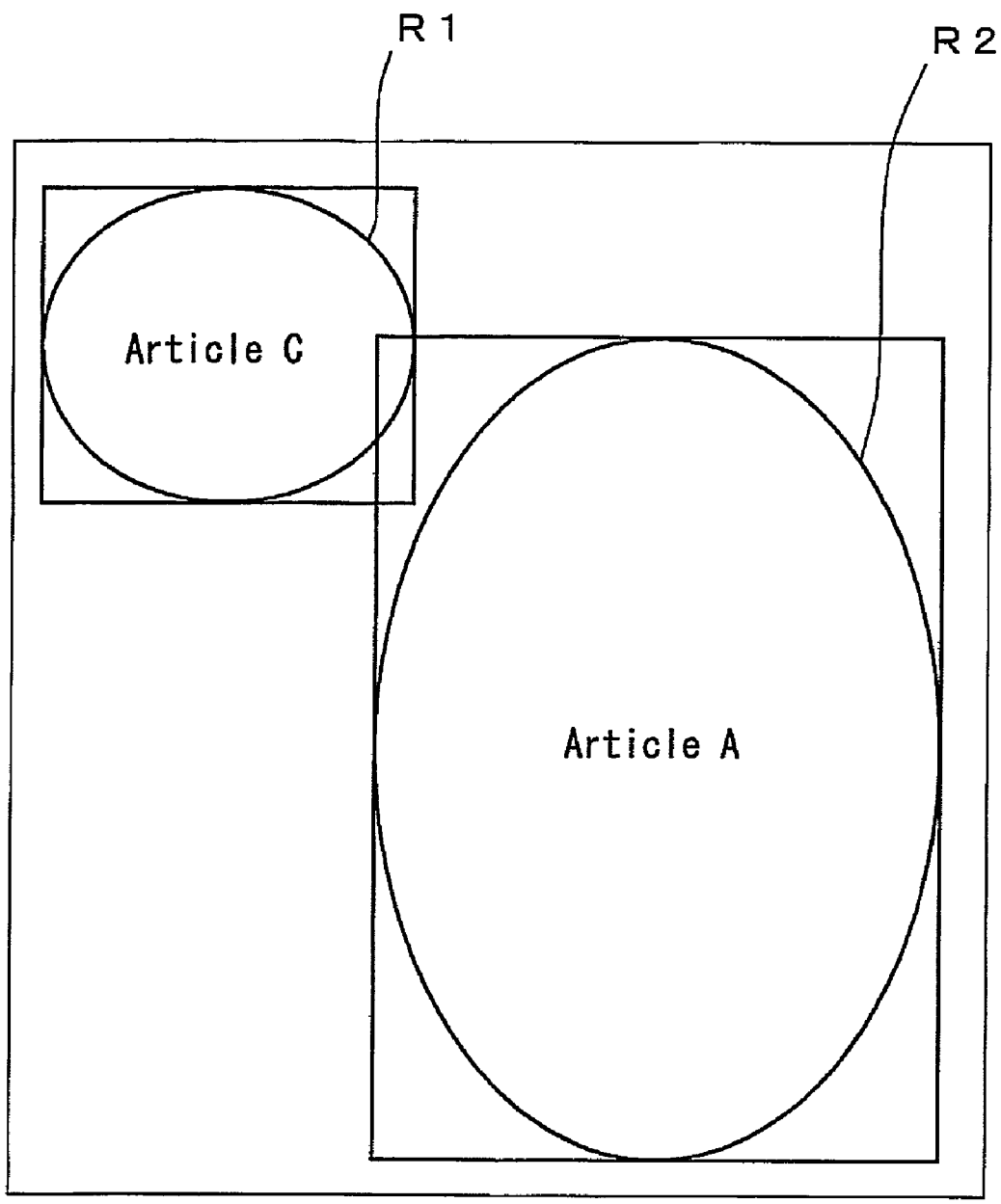
FIG. 13 is an illustration showing an example of a PCA diagram in which two examples of elliptic setting regions are described with a long axis of a first component and a short axis of a second component respectively.
Figure 14:
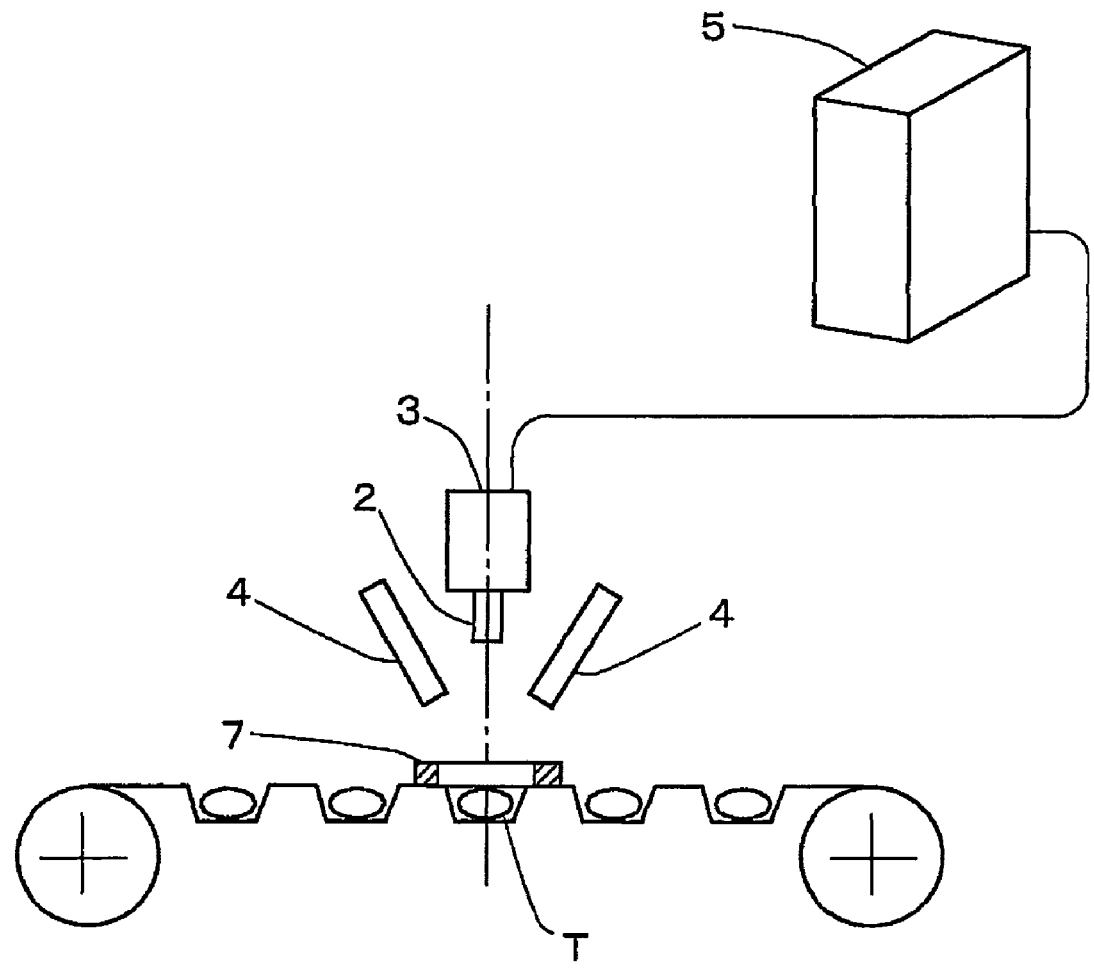
FIG. 14 is a side configuration view showing an embodiment of a different kind of object detecting apparatus (conveyer-type) using a plane spectrometer with respect to the present invention.
Figure 15:
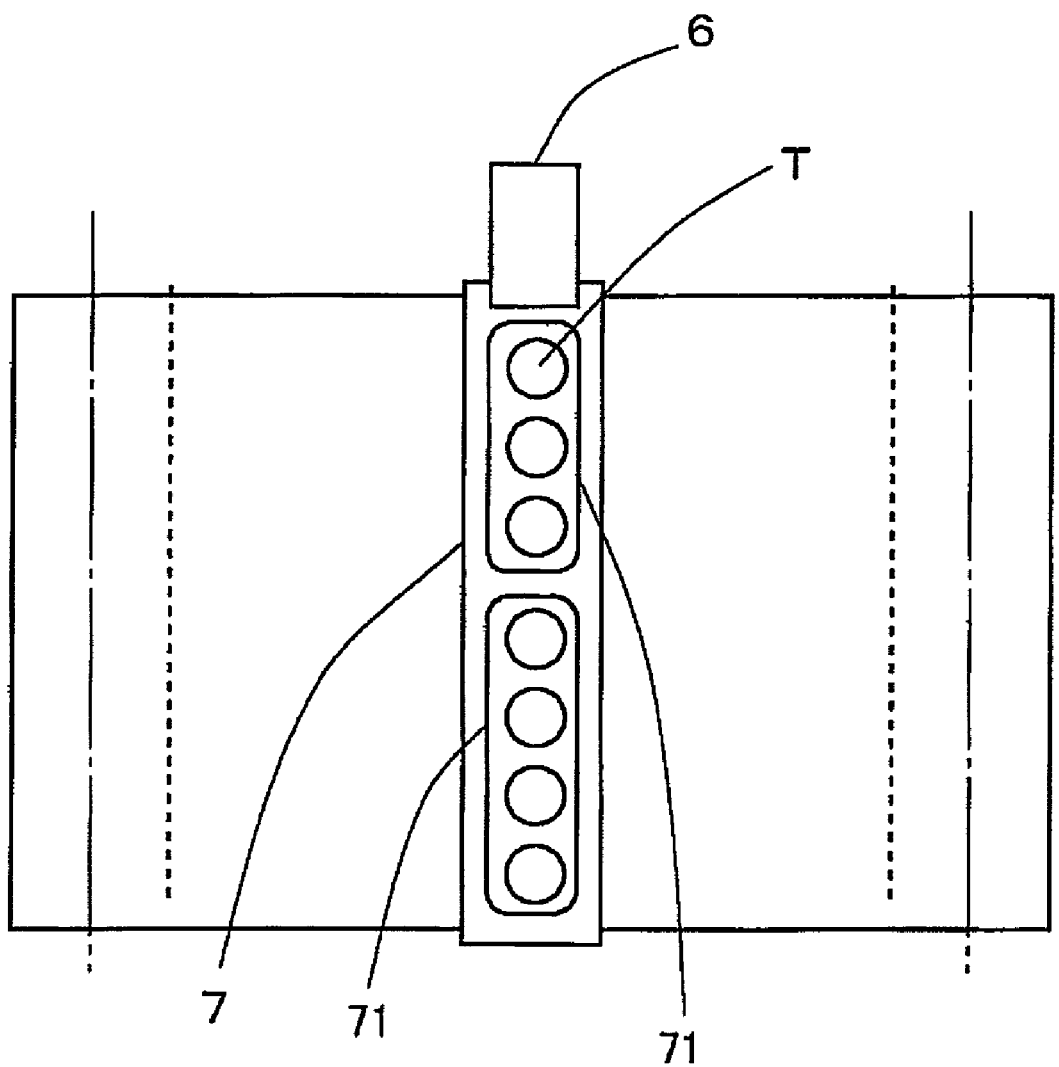
FIG. 15 is a plan configuration view of a main part of the aforementioned embodiment.
Figure 16A:
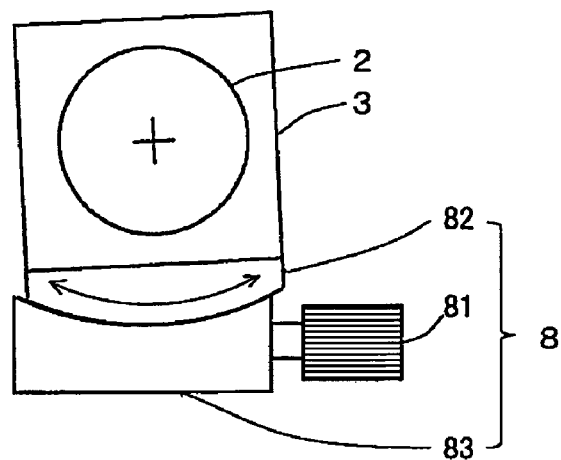
FIG. 16 is an explanatory view of a camera rotating mechanism.
Figure 16B:
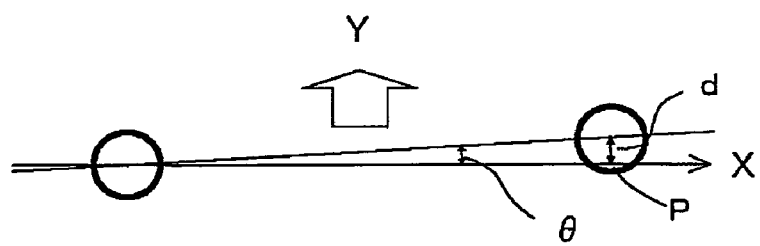
Figure 17:
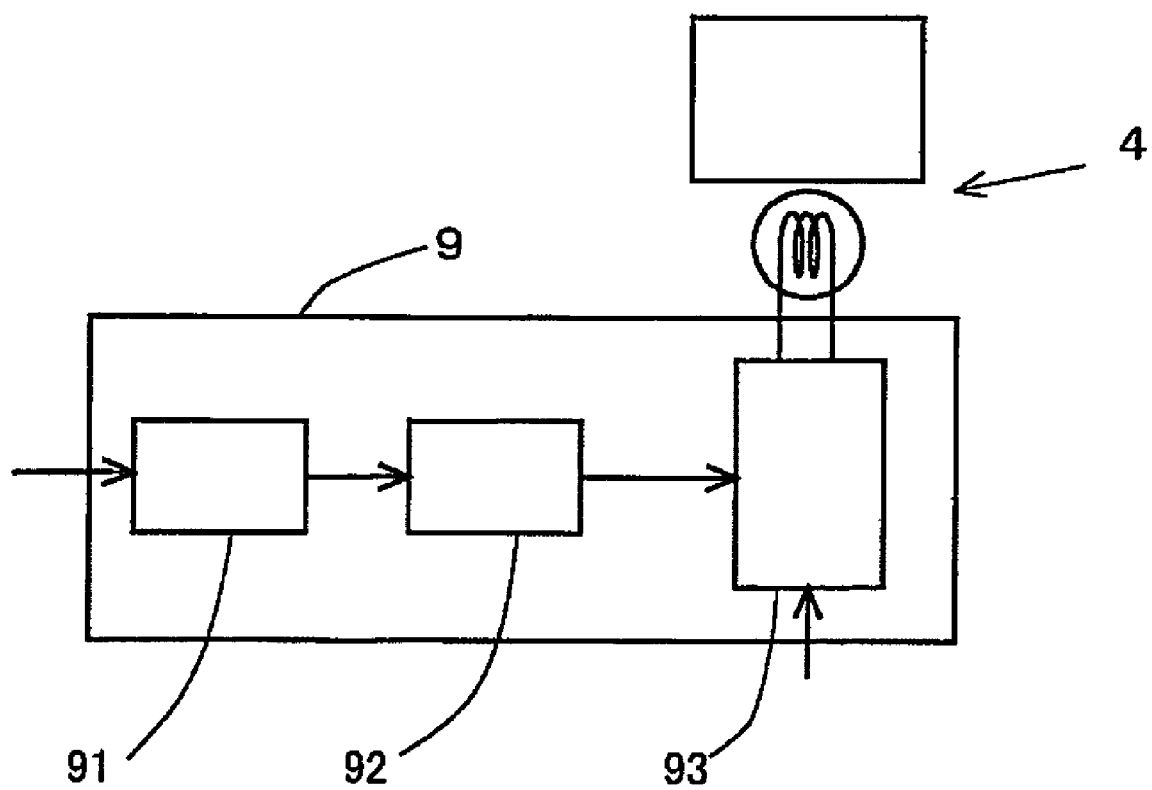
FIG. 17 is a block diagram of a correction circuit using a light volume compensator.
Figure 18A:
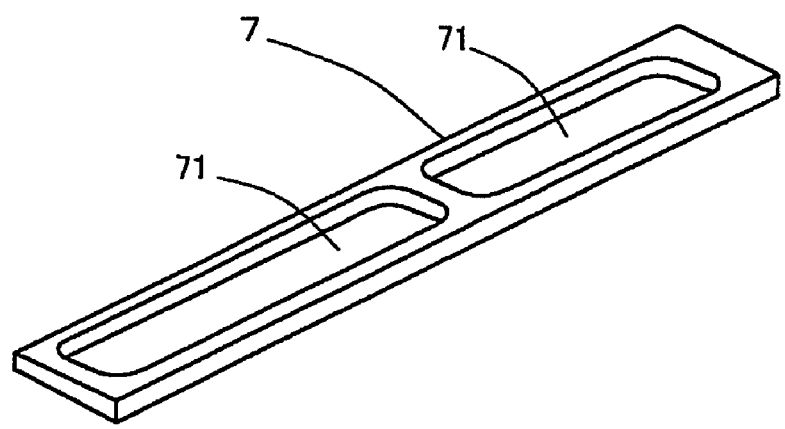
FIG. 18A is a perspective view thereof.
Figure 18B:
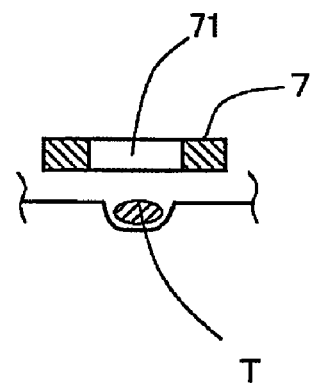
FIG. 18B is a side cross-section showing a using condition thereof.

REFERENCE NUMERALS 1 a different-kind-of-object detecting apparatus using a plane spectrometer
2 plane spectrometer
3 near-infrared ray camera
4 light guide
5 computer
6 light volume compensator
7 flutter-preventing plate
8 camera rotating mechanism
9 light volume correction circuit
11 adsorption drum-type conveying device
12 adsorption drum
13 conveyer-type conveying device
T object

The invention claimed is:

1. An apparatus for detecting a different kind of object among objects using a plane spectrometer, comprising
a conveyer means for conveying a plurality of objects;
an irradiating means for irradiating near-infrared rays to the plurality of objects conveyed by the conveyer means;
a plane spectrometer performing plane spectroscopy for a reflected light of near-infrared rays reflected from the plurality of objects, to which the near-infrared rays are irradiated with the irradiating means;
an imaging means for converting a plane spectrogram of the reflected light produced through the plane spectrometer into an electric signal by means of a near-infrared ray camera; and
an analyzing means for detecting a different kind of object from the plurality of objects using a method of main component analysis upon obtaining spectral data of the reflected light by means of analyzing the electric signal obtained with the imaging means,
wherein the analyzing means is configured to perform
a wavelength axis averaging processing for averaging spectral data in a direction of the wavelength axis;
an interpolation processing for interpolating the spectral data using Lagrangian secondary interpolation;
a measuring position optimization processing for detecting a center position of the object by detecting an edge of the object upon accumulating the spectral data in a direction of a spatial axis;
a spatial axis averaging processing for obtaining an average value of each wavelength at a plurality of points in a vicinity of the center position of the object detected by the measuring position optimization processing;
a differentiation processing for performing a first differentiation or a second differentiation for the spectral data;
a main component score calculation processing for calculating the main component score by calculating previously obtained loading vector data and the spectral data obtained from the above-listed processes; and
a determination processing for determining whether to be a different kind of object or a same kind of object on a basis of the calculated main component score.

2. The apparatus according to claim 1, wherein the wavelength axis averaging processing of the analyzing means performs at least any of a preprocessing for averaging the spectral data;

a preprocessing for standardizing the spectral data on a basis of a ratio of the spectral data to a predetermined value;

a preprocessing for standardizing the spectral data on a basis of a difference between the spectral data and a predetermined data; or the wavelength axis averaging processing for forming a moving average of the spectral data in the direction of the wavelength axis.

3. The apparatus according to claim 1, wherein the analyzing means is configured to perform a conversion processing for smoothing the spectral data.

4. The apparatus according to claim 1, wherein the analyzing means is configured to perform a correction processing for the spectral data by means of a MSC (Multiplicative scatter correction) method.

5. The apparatus according to claim 1, wherein the analyzing means is configured to detect abnormality of the object in a case that an edge exceeding a predetermined threshold cannot be detected in the measuring position optimization processing for detecting the center position of the object by detecting the edge of the object upon accumulating the spectral data in the direction of the spatial axis.

6. The apparatus according to claim 1, wherein the analyzing means is configured to perform the main component analysis for the object at each line being conveyed in multiple lines, using the loading vector data created at each line.

7. The apparatus according to claim 1, wherein the analyzing means is configured to perform the main component analysis selecting only data of a predetermined wavelength band in the spectral data.

8. The apparatus according to claim 1, wherein the analyzing means is configured to perform a conditional branching processing while repeating for two or more times upon changing a condition of the main component analysis.

9. The apparatus according to claim 1, wherein the imaging means is a rolling-type near-infrared ray camera, the rolling-type near-infrared ray camera having a camera rotating mechanism whereby the rolling-type near-infrared ray camera can be rotated around a shaft in parallel with a light axis thereof.

10. The apparatus according to claim 1, wherein the conveying means comprises a sheet-like conveying device for conveying objects, the sheet-like conveying device having a flap-inhibitor for preventing flap of the object by means of pressing a peripheral portion of the sheet-like conveying device around the object to be conveyed.

11. The apparatus according to claim 1, wherein a light volume compensator having a predetermined reflectance property is disposed at a position within a visual field of the imaging means.

* * * * *